United States Patent [19]

Stüwe et al.

[11] Patent Number: 5,141,525
[45] Date of Patent: Aug. 25, 1992

[54] PROCESS FOR PRODUCING HIGH-OCTANE, LOW-OLEFIN MOTOR FUELS AND MOTOR FUEL COMPONENTS

[75] Inventors: Arnd Stüwe, Leverkusen; Herbert Tschorn, Dormagen; Hans-Volker Scheef, Dormagen; Jörg-Uwe Michel, Dormagen, all of Fed. Rep. of Germany

[73] Assignee: Ec Erdolchemie GmbH, Kolen, Fed. Rep. of Germany

[21] Appl. No.: 687,269

[22] Filed: Apr. 18, 1991

[30] Foreign Application Priority Data

Apr. 28, 1990 [DE] Fed. Rep. of Germany ....... 4013711

[51] Int. Cl.$^5$ ................................................. C10L 1/18
[52] U.S. Cl. ........................................ 44/449; 44/447; 44/446; 585/264
[58] Field of Search ........................ 44/446, 447, 449; 585/264

[56] References Cited

U.S. PATENT DOCUMENTS

| | | | |
|---|---|---|---|
| 4,925,455 | 5/1990 | Harandi et al. | 44/449 |
| 4,950,820 | 8/1990 | Schleppinghoff et al. | 585/264 |
| 5,013,329 | 3/1991 | Bell et al. | 44/449 |
| 5,084,070 | 1/1992 | Kohler et al. | 44/449 |

FOREIGN PATENT DOCUMENTS

| | | |
|---|---|---|
| 0197348 | 10/1986 | European Pat. Off. . |
| 3538564 | 10/1986 | Fed. Rep. of Germany . |
| 3526443 | 2/1987 | Fed. Rep. of Germany . |

*Primary Examiner*—Brian E. Hearn
*Assistant Examiner*—M. Nuzzolillo
*Attorney, Agent, or Firm*—Sprung Horn Kramer & Woods

[57] ABSTRACT

High-octane, low-olefin motor fuels and motor fuel components having a content of alkyl tert.-alkyl ethers can be produced by reacting a crude hydrocarbon stream, which contains tertiary $C_5$-$C_8$-olefins in addition to saturated and olefinically, diolefinically and acetylenically unsaturated hydrocarbons in the same boiling range, simultaneously with one or more $C_1$-$C_4$-alkanols in a quantity from 0.5 to 5 mol per mol of the tertiary olefin(s) and with excess hydrogen relative to the total unsaturation under a pressure from 12 to 80 bar and at a temperature from 60° to 180° C. on a catalyst known per se or a mixture of catalysts known per se, which effect(s) both the etherification and the olefin hydrogenation.

19 Claims, No Drawings

PROCESS FOR PRODUCING HIGH-OCTANE, LOW-OLEFIN MOTOR FUELS AND MOTOR FUEL COMPONENTS

BACKGROUND OF THE INVENTION

1. Field of the Invention

The present invention relates to a process for producing motor fuels and motor fuel components from hydrocarbons which contain tertiary olefins in a mixture with saturated and olefinically, diolefinically and acetylenically unsaturated hydrocarbons, the tertiary olefins being etherified with one or more $C_1$-$C_4$-alkanols and the unsaturated constituents being largely hydrogenated.

2. Description of the Related Art

It has been known for a long time to react tertiary olefins with lower alkanols to give alkyl tert.-alkyl ethers. It is also known that, in the case of methyl tert.-butylether (MTBE), the equilibrium lies largely on the side of the ether at not unduly high temperatures, whereas even in the case of tert.-amyl methyl ether (TAME) at the same temperature, substantially smaller quantities of ether but, instead, considerable quantities of the starting materials methanol and tert.-amylenes are present. In the case of ethers from even higher tertiary olefins, the position of the equilibrium towards the ethers is even more unfavourable. It is also established specialist knowledge that such ethers are cleaved again into the starting materials at even higher temperatures. The formation and the cleavage of the ethers, that is to say the establishment of the equilibrium at the particular temperatures, are influenced by acidic catalysts which quite frequently can be the same for both the formation and the cleavage, the temperature being in each case adjusted to that favourable for the formation or decomposition. The selective etherification of the tertiary olefins has also already been utilized for converting cracked gasolines to higher-octane motor fuels and motor fuel components by the formation of such ethers. In this case, the monounsaturated and polyunsaturated constituents of the cracked gasoline remain in such motor fuels or motor fuel components.

The highly unsaturated constituents of such mixtures are gum formers. In connection with motor fuels, gum is understood as a content of oligomeric or polymeric materials in the fuel, which gum is expressed as the evaporation residue in the analysis of the motor fuels. The gum content in motor fuel leads not only to carbonization and to deposits in the combustion chamber of the engine, but also covers the pores of an etherification catalyst during the manufacture of such motor fuels, and hence reduces the activity of the catalyst and shortens its service life and in addition causes a yellow coloration of the motor fuel being formed.

A process has thus already been disclosed (DE-OS (German Published Specification) 3,538,564) which allows, simultaneously with the etherification of tertiary $C_5$-$C_8$-olefins present in crude hydrocarbon mixtures with $C_1$-$C_5$-alkanols, the highly unsaturated and highly reactive fractions, which are present in these crude hydrocarbon mixtures and are held responsible for the gum formation, to be hydrogenated by means of an addition of small quantities of hydrogen. Such a simultaneous etherification and hydrogenation under mild conditions is carried out on styrene/divinylbenzene resins which contain free sulphonic acid groups and elements of subgroups VI, VII or VIII of the periodic table of the elements, in the metallic state.

In the case of such a simultaneous etherification and partial hydrogenation of the highly unsaturated gum formers, the monoolefins remain in the reaction mixture. These monoolefins can be hydrogenated to the corresponding paraffins only under more severe reaction conditions. Such a hydrogenation is highly desirable, since the monoolefins, as sources of free radicals, are held responsible, in addition to other substances, for the damage to the ozone layer in the upper atmosphere. A still persisting high olefin content in the motor fuels used worldwide on a large scale must therefore, according to present understanding, increasingly contribute to the undesired further damage to this ozone layer. There has therefore been no lack of attempts to convert the olefins in the motor fuels as far as possible into the corresponding paraffins by hydrogenation. Since, according to expert knowledge, a hydrogenation of the monoolefins was feasible only under more severe conditions, such as higher temperature, higher hydrogen availability and higher pressure, destruction of the ethers, which increase the octane number and are therefore desired, of the tertiary olefins had always to be expected. Such a destruction was all the more to be feared, since the involvement of the catalyst supports, frequently rendered acidic, of the hydrogenation catalysts to be employed had also to be taken into consideration. Effective hydrogenation processes for the monoolefins while preserving the alkyl tert.-alkyl ethers therefore had to proceed under special conditions. Thus, DE-OS (German Published Specification) 3,526,443 describes a hydrogenation process for olefinic hydrocarbons, which are present as a mixture with alkyl tert.-alkyl ethers, wherein very specific catalysts are used which possess a hydrogenation-active component on a catalyst support having a specific surface area of more than 50 $m^2/g$ and a pore diameter of predominantly < 1000 nm.

From the expert understanding and in the knowledge of the prior efforts for successfully carrying out the etherification on the one hand and, on the other hand, the extensive hydrogenation of the olefins while preserving the ethers already formed, it was not to be expected that, beyond the easily feasible partial hydrogenation of only the highly unsaturated compounds during the etherification, extensive hydrogenation of the monoolefins which are more difficult to hydrogenate could also be carried out, in which case it was necessary to meet the following requirements:

1. the monoolefins without a tertiary carbon atom, which are present, should be extensively hydrogenated without hydrogenation of the tertiary olefins to be etherified so that the maximum possible yield of alkyl tert.-alkyl ether is achieved;
2. the more severe reaction conditions, which also include a higher hydrogenation temperature than that for the partial hydrogenation, should not lead to a cleavage of ethers, once formed, into the starting products alkanol and tertiary olefin; and
3. the highly exothermic heat of reaction of the hydrogenation should not lead to overheating of the reaction mixture, which would reinforce the trends listed under 2., which had to be feared.

SUMMARY OF THE INVENTION

Surprisingly, it has now been found that, contrary to the existing fears, an increase in the hydrogen availability under an increased pressure does not impair the etherification of the tertiary olefins and that an undesired hydrogenation of the tertiary olefins, which are to be etherified, virtually does not take place at all when the etherification and hydrogenation are carried out simultaneously.

The invention therefore relates to a process for producing high-octane, low-olefin motor fuels and motor fuel components having a content of alkyl-tert.-alkyl ethers, which is characterized in that a crude hydrocarbon stream, which contains tertiary $C_5$-$C_8$-olefins, preferably tertiary $C_5$-$C_7$-olefins, in addition to saturated and olefinically, diolefinically and acetylenically. unsaturated hydrocarbons in the same boiling range, is reacted simultaneously with one or more $C_1$-$C_4$-alkanols, preferably $C_1$-$C_2$-alkanols and particularly preferably methanol, in a quantity from 0.5 to 5 mol, preferably 0.8 to 2.5 mol and particularly preferably 1 to 2 mol, per mol of the tertiary olefin(s), and with hydrogen in excess relative to the total unsaturation under a pressure from 12 to 80 bar, preferably 15 to 60 bar and particularly preferably 15 to 35 bar, and at a temperature from 60 to 180° C., preferably 70 to 140° C. and particularly preferably 70 to 120° C., on a catalyst known per se or on a mixture of catalysts known per se, which effect(s) both the etherification and the olefin hydrogenation.

DETAILED DESCRIPTION OF THE INVENTION

The process according to the invention is distinguished by the following advantageous effects:

1. the highly unsaturated gum formers are eliminated by the hydrogenation and, therefore, are neither present in the motor fuel nor able to deactivate the catalyst(s) employed by deposition;
2. the ethers formed by etherification of the tertiary olefins increase the knock resistance of the motor fuels being formed (increase in octane number);
3. the monoolefin content is very greatly reduced, harmful effects on the environment being eliminated;
4. the reduction in both the highly unsaturated and monoolefinically unsaturated compounds gives lower colour numbers in the motor fuel obtained;
5. the paraffins formed from the unsaturated compounds are distinguished by a lower vapour pressure, as compared with the originally unsaturated compounds, which leads to a lower volatility which in turn is desirable for reasons of protecting the environment; and
6. the extensive reduction in all the unsaturated compounds gives, furthermore, a desirable reduction in the sensitivity, that is to say a reduction of the distance between the motor octane number (MON) and the research octane number (RON). The sensitivity falls from values of about 18 to 20 to values of about 10 to 12.

As examples of tertiary olefins, those may be mentioned which contain 5 to 8, preferably 5 to 7 carbon atoms; tertiary $C_5$- and/or $C_6$-olefins are particularly preferred. Such tertiary olefins are present in the crude hydrocarbon streams to be converted according to the invention essentially as a mixture of several thereof. Moreover, such hydrocarbon streams can always contain saturated or unsaturated hydrocarbons having adjacent carbon numbers. For example, a hydrocarbon mixture which essentially contains tertiaryamylenes, in general contains small quantities of i-butene and/or tertiary hexenes.

As nontertiary olefins, for example $C_5$-$C_9$-olefins of straight-chain, cyclic and/or branched type are present, preferably those which contain 5 to 7 carbon atoms, and particularly preferably again those which represent $C_5$-and/or $C_6$-olefins. These olefins, too, are present in the crude hydrocarbon mixtures to be converted according to the invention essentially as a mixture of several thereof. For example, a hydrocarbon stream with tertiary amylenes equally also contains n-pentenes and cyclopentene. Moreover, such crude hydrocarbon mixtures contain constituents which form, under the reaction conditions, oligomeric or polymeric substances which are known as gum to those skilled in the art. These gum formers are, for example, diolefins and/or acetylenic and/or olefinic-acetylenic compounds. The saturated straight-chain or branched or cyclic hydrocarbons of the same boiling range are likewise found in association with the said unsaturated compounds.

Hydrocarbons of the said type are available in petrochemical plants and/or refineries. They can be obtained, for example, in the conversion of naphtha, liquid petroleum gas (LPG), crude oil distillates, gas oils or other starting hydrocarbon mixtures in steam crackers, catalytic crackers, isomerization plants or dehydrogenation plants. They can be employed according to the invention either as such with a greater range of carbon atom numbers or as narrower distillation cuts, in which case, for example, the distillation cuts essentially containing $C_5$- or $C_6$-hydrocarbons contain small fractions of the adjacent $C_4$- and/or $C_7$-homologues. Typical compositions of $C_5$-distillation cuts from steam crackers or catalytic crackers are approximately the following:

| Substance, % by weight (approx.) | Steam cracker | Cat. cracker |
| --- | --- | --- |
| $C_4$/light ends | 1–5 | 1–5 |
| n-/i-pentane | 20–30 | 30–35 |
| n-pentene | 15–20 | 25–30 |
| 3-methyl-1-butene | 0.5–3 | 0.5–2 |
| 2-methyl-1-butene | 5–10 | 7–11 |
| 2-methyl-2-butene | 8–17 | 15–20 |
| cyclopentane | 4–6 | 1–3 |
| cyclopentene | 20–27 | 2–5 |
| diolefins/acetylenes | 0.5–5 | 0.5–5 |

A typical hydrocarbon stream for the process according to the invention is represented by the so-called benzene light ends which are formed after the $C_4$ hydrocarbons have been separated off and before aromatics are isolated.

Examples of alkanols for the process according to the invention which may be mentioned are primary or secondary alkanols, preferably primary alkanols having 1 to 4 carbon atoms and preferably 1 to 2 carbon atoms. The use of methanol is very particularly preferred. The alkanols are employed in a quantity from 0.5 to 5 mol, preferably 0.8 to 2.5 mol and particularly preferably 1 to 2 mol, per mol of the tertiary olefin(s).

The process according to the invention is characterized in particular by the use of excess hydrogen relative to the total unsaturation of the crude hydrocarbon streams to be employed. The total unsaturation comprises the content of all olefinic and acetylenic multiple bonds, each acetylenic bond being counted as two olefinic bonds. The total unsaturation can be determined analytically in a known manner and expressed as mol of total unsaturation per volume unit or weight unit of the hydrocarbon stream. Excess hydrogen means, for example, 1.5 to 20 mol, preferably 2 to 8 mol of hydrogen per mol of total unsaturation.

Hydrogen can be employed in the pure form or in a technical form. As an economic advantage, a hydrogen can be employed which arises in petrochemical plants and is associated with methane and/or nitrogen. The $H_2$ concentration in such a pure or technical hydrogen is 70 to 100% by volume of $H_2$, and it is frequently 80 to 90% by volume of $H_2$ in $H_2$-containing residual gases from petrochemical plants.

A further particular characteristic of the process according to the invention is the increased pressure under which it is carried out. This pressure is 12 to 0 bar, preferably 15 to 60 bar and particularly preferably 15 to 35 bar.

For the extensive hydrogenation of even the monoolefins, the process according to the invention is carried out at a temperature which tends to be higher than that which would be necessary for the partial hydrogenation of only the highly unsaturated compounds, for instance according to DE-OS (German Published Specification) 3,538,564. This temperature is in the range from 60 to 180° C., preferably 70 to 140° C. and particularly preferably 70 to 120° C. In a very particularly preferred manner, the process is operated in the range from 80 to 110° C.

The process according to the invention is carried out on a catalyst or a mixture of catalysts which effect(s) both the etherification and the olefin hydrogenation. Such catalysts are known to those skilled in the art. In a preferred manner, these are heterogeneous catalysts, from which the reaction product can easily be separated off. Thus, the starting point can be a catalyst which contains both acidic groups effecting the etherification and hydrogenation-active catalyst constituents However, it is also possible to start from a catalyst mixture, of which one constituent carries only the acidic groups necessary for the etherification, whereas the other constituent contains only the hydrogenation-active component. In every case, care must be taken to ensure that the hydrogenation-active component or the constituent of a catalyst mixture, which carries the hydrogenation-active component, does not wholly or partially cleave again the resulting ether in an undesired manner. Examples of catalysts and mixtures of catalysts which can be used for this purpose are:

Macroporous and/or gel-type cation exchangers which contain a hydrogenation-active component and at the same time are present in the $H^+$ form.

Hydrogenation catalysts, which are known to those skilled in the art are Pd, Ni, Pt, Rh, Os, Ir and the like on $Al_2O_3$, $SiO_2$, spinel, mixtures thereof or on further known supports, if they have an acidity sufficient to effect the etherification reaction.

Mixtures of acidic ion exchangers with hydrogenation catalysts (which may be acidic) are possible.

In a procedure using two or more reactors, it is also possible to employ in the first reactor a catalyst or a mixture of several catalysts, which both have a hydrogenation-active component and are sufficiently acidic, whereas catalysts having merely acidic properties, for example cation exchangers in the $H^+$ form, are employed in the second (following) reactor(s).

In a preferred manner, the cation exchangers in the $H^+$ form, which are already known from the etherification of tertiary olefins with alkanols, are suitable for the process according to the invention, if they are additionally loaded with one or more metals from subgroups VI and/or VII and/or VIII of the periodic table of the elements, in the elemental form. Such cation exchangers can have a macroporous or gel-type structure and have been produced by copolymerization of vinyl monomers and divinyl crosslinking agents, if appropriate in the presence of solvents, or by condensation of phenol and formaldehyde. Vinyl monomers are, for example, styrene or acrylic acid esters; an example of divinyl crosslinking agents is divinylbenzene. The degree of crosslinking, calculated as % by weight of divinyl crosslinking agents, is 2 to 65%, preferably 8 to 25%. The acidic groups of such cation exchangers are, for example, carboxyl groups, phosphoric acid groups or sulphonic acid groups. In a preferred manner, cation exchangers in the $H^+$ form, containing strongly acidic sulphonic acid groups, are employed. In a further preferred manner, these are styrene/divinylbenzene polymers which carry such sulphonic acid groups and are commercially available under various descriptions. The specific surface area of such cation exchangers for the process according to the invention is 5 to 750 $m^2/g$, preferably 50 to 250 $m^2/g$, measured on the dry exchanger resin. The mean pore radius of the cation exchangers is 50 to 1200 Å, preferably 70 to 500 Å. The cation exchangers are, for example, in the form of bead polymers having particle sizes from 0.1 to 2 mm or in the form of a powder resin in particle sizes from 10 to 100 $\mu$m. However, different particle sizes can also be employed. The handling of such cation exchangers is known to those skilled in the art from the ion exchanger technology and/or catalyst technology.

The following may be mentioned as metals for the loading of the cation exchangers: chromium, molybdenum, tungsten, manganese, rhenium, iron, cobalt, nickel, ruthenium, rhodium, palladium, osmium, iridium and platinum. In a preferred manner, palladium, platinum, rhenium, molybdenum, nickel, tungsten and cobalt may be mentioned; in a particularly preferred manner, palladium, platinum and nickel may be mentioned. These metals can be applied to the cation exchanger individually or as a mixture of several thereof. In a preferred manner, only one of the said metals is employed.

The loading of the cation exchangers with one or more of the said metals can be effected, for example, in such a way that a non-complex, cationic salt of these metals is brought together in a manner known per se with the cation exchanger in the $H+$ form. In this case, the metal cation is absorbed on the cation exchanger by an ion exchange mechanism. The acid thus released is, if necessary, neutralized by suitable compounds having an alkaline reaction, for example alkali metal hydroxide solution. The quantity of the metal salts to be applied is calculated or determined by simple preliminary experiments, so that the desired quantity of metals is applied to the cation exchanger. This quantity is 0.001 to 10 g, preferably 0.2 to 3 g, relative to 1 l of dry cation exchanger.

The metal-doped cation exchanger is washed until neutral, dried, for example at 80 to 100° C. in vacuo, and then treated with hydrogen for converting the applied metals into the elemental state, for example, at 2 to 50 bar, preferably at 10 to 30 bar $H_2$ pressure and at a temperature from 50 to 150° C., preferably 70 to 120° C. In principle, other reducing agents, such as hydrazine, formaldehyde or formic acid, can also be used.

Such a metal-loaded cation exchanger in the H form contains simultaneously the acidic groups for etherification and the hydrogenation-active component. These preferably employed, metal-loaded cation exchangers in the $H^+$ form give a higher yield of alkyl tert.-alkyl ethers than that corresponding to the content of tertiary olefins in the crude hydrocarbon stream to be converted. This can be explained only in such a way that olefins which are branched but not tertiary undergo an isomerization which shifts the double bond to the branching point, so that a tertiary olefin is formed which can then likewise enter the etherification reaction. This surprising process variant, using a metal-loaded cation exchanger in the $H^+$ form, shows that, during the extensive hydrogenation of even the monoolefins (in addition to the hydrogenation of the highly unsaturated compounds), not only the tertiary olefins are protected from the concomitant hydrogenation, but that in addition branched olefins, which can be isomerized to tertiary olefins, are likewise protected from hydrogenation and can hence undergo an isomerization and subsequent etherification in the manner described.

The metal-doped cation exchanger described in the $H^+$ form can also be blended as a mixture with a cation exchanger in the $H^+$ form, which is not loaded with metals, and employed according to the invention as such a mixture. The mixture of a cation exchanger in the $H^+$ form, which is not loaded with metals, can be carried out in a wide range from 1 to 90% by volume, relative to the mixture of the loaded and non-loaded cation exchanger. Such a blend serves above all for reducing the costs, since the cation exchanger loaded with metals is considerably more expensive than the non-loaded cation exchanger. To achieve this aim, it is therefore appropriate to employ, for example, 40 to 90% by volume, preferably 55 to 75% by volume, relative to the total mixture, of the cation exchanger in the $H^+$ form, which is not loaded with metals.

The catalyst or the catalyst mixture is subjected to a loading of $a=0.1$ to 100, preferably 0.3 to 20 and particularly preferably 0.5 to 5. The symbol "a" here denotes kilograms of crude hydrocarbon mixture containing tertiary olefins, diolefins, monoolefins and paraffins, per litre of catalyst volume per hour.

In the process according to the invention, the crude hydrocarbon stream and the alkanol are present in the liquid phase. The catalyst or the catalyst mixture are arranged in a fixed bed, for example in a shaft reactor or tube reactor. The liquid feed materials can here flow upwards into the catalyst bed or vice versa. The hydrogen is fed to the liquid feed materials in co-current or in counter-current. Running both the liquid feed materials and the hydrogen in co-current is preferred here.

The hydrogenation is an exothermic reaction, which makes accurate control of the temperature profile indispensable in the process according to the invention, in which not only an extensive hydrogenation even of all monoolefins is desired, but this extensive hydrogenation of the monoolefins must also be carried out at a temperature level which tends to be higher than that in the hydrogenation of only the highly unsaturated compounds. For this purpose, it can be advantageous and also represents a preferred variant to carry out the process according to the invention in a plurality of series-arranged reactors, preferably in two reactors. In addition, a part of the reaction mixture flowing out of the first reactor can be taken off and recycled to the reactor inlet of this first reactor, whereas the part of the reaction mixture, which has not been taken off, is passed into a second reactor or into further reactors. The part of the reaction mixture, which is taken off and recycled to the reactor inlet, can be passed through a cooler on the recycling path, in order to remove heat of reaction from the system.

A further advantageous variant of the reaction method comprises feeding the hydrogen at various points of the reactor or into various reactors of a reactor system consisting of a plurality of reactors. Moreover, it can be advantageous, especially in the case of divided hydrogen feed, to use catalyst mixtures, if these are used, of different composition in individual sections of one reactor or in different reactors, if the process is operated with a plurality of reactors, in different composition with respect to the hydrogenation-active component and the acidic component. Thus, for example, when a mixture of cation exchanger loaded with metals and cation exchanger not loaded with metals is used, it can be advantageous, in the case of a plurality of series-arranged reactors, initially to employ in the first reactor a smaller proportion of the cation exchanger loaded with metals in the mixture than in the second reactor or in the following reactors.

The process according to the invention will be explained by way of example by reference to the attached FIG. 1, as follows: the crude hydrocarbon mixture (1), the alkanol(s) (2) and hydrogen (3) are fed as feed streams, after passing through a preheater (4) and a mixer (5), to the reactor (6) which is at least partially charged with the cation exchanger in the $H^+$ form loaded with metals, and reacted therein. After leaving the reactor (6), a part of the reaction product can be recycled (7) for heat removal. After passing through a second reactor (8), in which further hydrogen (9) can be added if necessary, the reaction product passes into the stabilizer column (10). In (10), residual gas, predominantly excess hydrogen and any methane or nitrogen which may be present, is taken off over the top as stream (11). The two reactors (6) and (8) can also be structurally combined and operated as one reactor system. (10) is heated by a circulation heater (13). A part of the circulating bottom stream is taken off as a gum-free, low-olefin, colourless motor fuel or motor fuel component (12) having a lower vapour pressure and containing alkyl tert.-alkyl ether. The term "green gasoline" has been formed in parlance for such a motor fuel or such a motor fuel component.

The motor fuels and motor fuel components which can be produced according to the invention are distinguished by a residual bromine number, as an expression of the remaining unsaturation, from 5 to 40, preferably 10 to 30 g of $Br_2/100$ g, whereas the crude hydrocarbon streams fed have bromine numbers of about 100 and higher. The higher content of paraffins, as compared with the crude hydrocarbon stream as the feed material, is reflected in a reduction of the vapour pressure. The extent of the octane number increase is of course dependent, in a manner familiar to those skilled in the art, on the quantity of the etherifiable tertiary olefins in the crude hydrocarbon stream and also on the extent of the etherification actually carried out which, inter alia, depends on the molar quantity of alkanol. The extent of the reduction in unsaturation (characterized by the decrease in bromine number) is dependent on the setting of the temperature, of the hydrogen rate and of the pressure, and is familiar to those skilled in the art.

The increase in yield of alkyl tert.-alkyl ether by the isomerization of olefins which are branched but not tertiary, and the reduction in sensitivity have already been mentioned above. At a content of etherifiable olefins in the crude starting hydrocarbon from 10 to 30% by weight, an alkyl tert.-alkyl ether content of about 12 to 42% by weight is to be expected in the reaction mixture according to the invention. The isomerization, which has been mentioned, of the branched olefins which are not tertiary takes place under the indicated conditions of the process according to the invention in such a way that the ether yield can be raised by 1 to 10 percentage points, depending on the concentration of such compounds in the crude hydrocarbon mixture. The sensitivity falls from about 14 to 16 down to 10 to 12, and the APHA colour number is always below 8, frequently below 5 and can reach values below 4.

Furthermore, the motor fuels and motor fuel components produced according to the invention contain only gum formers, so that reliable adherence to, and even lower values than, the maximum quantity of gum (measured as the evaporation residue) of 5 mg/100 ml, laid down in DIN 51 607 and in DIN 51 600 and/or in the ASTM standard for automotive gasoline, is ensured. Due to the always present excess of hydrogen in the production, according to the invention, of motor fuels and motor fuel components and due to the resulting prevention of gum formation, not only the service life of the catalyst, in particular the service life of the cation exchanger in the $H^+$ form loaded with metals, is substantially extended, but, a constant high conversion over a long period is achieved due to the simultaneous prevention of deposition on the active centres of the catalyst. Thus, the service life of a cation exchanger in the $H^+$ form loaded with metals is extended from about 8 months without the additional use of hydrogen to at least 2 years reached so far, this catalyst being still in use.

The motor fuels and motor fuel components obtained according to the invention and having a content of alkyl tert.-alkyl ether can, if this is desired, be separated by distillation in a manner known to those skilled in the art, for example in order to be able to pass the thus obtainable parts of the motor fuels and motor fuel components separately and specifically to other motor fuels or motor fuel components or also to other uses. In the case of processing by distillation, the following fractions, for example, of the reaction products produced according to the invention can be obtained (a) the residual gas and the hydrocarbons as the top stream; (b) a stream containing mainly the alkyl tert.-alkyl ether (for example TAME from a $C_5$ cut) as a side stream and (c) a gum-free bottom stream which contains higher ethers and other high-boilers.

EXAMPLE 1

Preparation of a catalyst mixture, to be employed according to the invention from cation exchangers Such a quantity of palladium acetate was made available to a commercially available styrene/divinyl copolymer having sulphonic acid groups (Lewatit SPC 118® from Bayer AG) in the water-moist $H^+$ form that 1 g of Pd per litre of dry resin was present on the cation exchanger after reduction with $H_2$. The acid released in the treatment with palladium acetate was neutralized with 1% by weight strength NaOH. The cation exchanger washed until neutral was dried for 24 hours at 100° C. in a water pump vacuum. The palladium present on the cation exchanger was reduced to the metal within 48 hours at 90 to 100° C. and 20 to 25 bar $H_2$ pressure. The Pd-loaded cation exchanger thus prepared was employed as a catalyst system in a mixture with the cation exchanger (likewise Lewatit SPC 118®) not loaded with metal, in a 1:1 volume ratio.

EXAMPLE 2

The catalyst mixture obtained according to Example 1 was employed in the following manner in a temperature-controllable, continuous-flow laboratory apparatus consisting of 2 double-jacket reactors: the first continuous-flow reactor of 25 ml internal width and having temperature measurement points at intervals of 100 mm was filled with 200 ml of Pd-containing, strongly acidic cation exchanger; in the same way, the downstream 2nd reactor of the same dimensions was charged with undoped acidic cation exchanger. The crude hydrocarbon mixture employed was the $C_5$ stream from a steam cracker (so-called aromatic light ends) having a content of 11.6% by weight of 2-methyl-2-butene, 2.6% by weight of 2-methyl-1-butene (these two are tertiary olefins) and 1.1% by weight of 3-methyl-1-butene (non-tertiary olefin). Apart from $C_5$-hydrocarbons, the feed product additionally contained a quantity of about 21% by weight of $C_6$-hydrocarbons. The bromine number of this feed product was 105, the MON was 7 and the RON was 91. The boiling range was 35 to 65° C.; the vapour pressure at 38° C. (Reid Vapour Pressure = RVP) was 0.97 bar. The diolefin content was 0.38%. The loading of the catalyst was set to $a=1$ and the pressure was set to 22 bar. The temperature of the first reactor was maintained at 90 to 95° C., and that of the second reactor at 65° C. The hydrocarbon mixture was mixed, in a mixing chamber upstream of the reactor, with the stoichiometric quantity of methanol, relative to etherifiable olefins, and preheated. The added rate of hydrogen was adjusted such that an exit gas rate of 160 l/h per litre of catalyst was maintained.

The reaction product obtained was a colourless, virtually diolefin-free, ether-containing motor fuel component: APHA colour number < 5; dienes < 0.01% by weight; 14.0% by weight of TAME and 1.5% by weight of higher tertiary ethers. 0.5% by weight of the 3-methyl-1-butene was converted by isomerization and etherified. The olefinic fraction was reduced by more than two thirds, whereby a $BR_2$ number of 34 resulted. The MON was increased to 81.4, and the RON to 92.4, from which a sensitivity of 11 resulted. Vapour pressure was 0.84 bar (RVP); the evaporation residue was 1 mg/100 ml.

EXAMPLE 3

The experiment was carried out as in Example 2, but the reaction product was already taken off after the 1st etherification reactor, which was charged exclusively with Pddoped cation exchanger; the loading was set to $a=1$. A reaction product comparable to Example 2 was obtained.

EXAMPLE 4

The experiment was carried out as in Example 2, but the catalyst system was divided in such a way that in each case one half of the two reactors was charged with Pd-doped cation exchanger in the lower part and the other half was charged with undoped ion exchanger. For a more favourable distribution of the heat of reaction, the hydrogen was fed to the two reactors in a ratio of 1:1. In this procedure again, a reaction product corresponding to Example 2 was obtained.

EXAMPLE 5

For Comparison

The experiment was carried out as in Example 2, but without addition of $H_2$. The reaction product containing 13.4% by weight of TAME was coloured yellow, had an APHA colour number of about 2500 and an evaporation residue of 20 mg/100 ml. The octane number values were below those from Example 2. The vapour pressure and olefin content ($Br_2$ number = 80) were above the values from Example 2.

EXAMPLE 6

For Comparison

The experiment was carried out as in Example 2, but the hydrogen rate employed was set to 20 l of $H_2$ per litre of catalyst, and the reactor temperatures were 75° C. in the 1st and 70° C. in the 2nd reactor. The pressure was set to 15 bar. The reaction product obtained was a colourless motor fuel component with 14.0% by weight of TAME. The APHA colour number was < 5, and the evaporation residue was 1 mg/100 ml. However, the bromine number was about 80; the vapour pressure was 0.9 (RVP); the MON value was 79.5 and the RON value was 92.8, from which a sensitivity of 13.3 results.

What is claimed is:

1. A process for producing high-octane, low-olefinic motor fuels and motor fuel components having a content of alkyl tert.-alkyl ethers, from a crude hydrocarbon stream, which contains tertiary $C_5$-$C_8$-olefins in addition to saturated and olefinically, diolefinically and acetylenically unsaturated hydrocarbons in the same boiling range, wherein said crude hydrocarbon stream is reacted simultaneously with one or more $C_1$-$C_4$-alkanols in a quantity from 0.5 to 5 mol per mol of the tertiary olefin(s), and with hydrogen in excess relative to the total unsaturation, under a pressure from 12 to 80 bar and at a temperature from 60 to 180° C. on a catalyst or on a mixture of catalysts, which effect(s) both the etherification and the olefin hydrogenation to effect the relatively complete hydrogenation of the compounds other than the tertiary $C_5$-$C_8$ olefins.

2. The process of claim 1, wherein the crude hydrocarbon stream contains tertiary $C_5$-$C_7$-olefins.

3. The process of claim 1, wherein the crude hydrocarbon stream is reacted with one or more $C_1$-$C_2$-alkanols.

4. The process of claim 3, wherein the crude hydrocarbon stream is reacted with methanol.

5. The process of claim 1, wherein the alkanol quantity is 0.8 to 2.5 mol per mol of tertiary olefin(s).

6. The process of claim 5, wherein the alkanol quantity is 1 to 2 mol per mol of tertiary olefin(s).

7. The process of claim 1, wherein the reaction is carried out under a pressure of 15 to 60 bar.

8. The process of claim 7, wherein the reaction is carried out under a pressure of 15 to 35 bar.

9. The process of claim 1, wherein the reaction is carried out at a temperature from 70 to 140° C.

10. The process of claim 9, wherein the reaction is carried out at a temperature from 70 to 120° C.

11. The process of claim 1, wherein the catalyst used is a gel-type or macroporous cation exchanger in the $H^+$ form, which contains 0.001 to 10 g of one or more metals of subgroups VI and/or VII and/or VIII of the periodic table of the elements in the elemental form per litre of dry cation exchanger and has a degree of crosslinking from 2 to 65% and a specific surface area from 5 to 750 $m^2/g$ of dry exchanger resin.

12. The process of claim 11, wherein the cation exchanger has a degree of crosslinking of 8 to 25%.

13. The process of claim 11, wherein the cation exchanger contains one or more metals selected from the group consisting of palladium, platinum, rhenium, molybdenum, nickel, tungsten and cobalt.

14. The process of claim 13, wherein the cation exchanger contains one or more metals from the group consisting of palladium, platinum and nickel.

15. The process of claim 1, wherein hydrogen is employed in a quantity from 1.5 to 20 mol per mol of total unsaturation.

16. The process of claim 15, wherein hydrogen is employed in a quantity from 2 to 8 mol per mol of total unsaturation.

17. The process of claim 11, wherein the cation exchanger in the $H^+$ form, loaded with metals, is employed as a mixture with a cation exchanger in the $H^+$ form, not loaded with metals.

18. The process of claim 1, which is operated in a plurality of series-arranged reactors.

19. The process of claim 18, which is operated in 2 series-arranged reactors.

* * * * *